United States Patent
Kaye et al.

(10) Patent No.: US 7,942,927 B2
(45) Date of Patent: May 17, 2011

(54) TREATING VALVE FAILURE

(75) Inventors: David Martin Kaye, Beaumaris (AU);
John Melmouth Power, Williamstown (AU); Clifton A. Alferness, Port Orchard, WA (US); Adam Lucas Bilney, Wy Yung (AU)

(73) Assignee: Baker Medical Research Institute, Prahan, Victoria (AU)

( * ) Notice: Subject to any disclaimer, the term of this patent is extended or adjusted under 35 U.S.C. 154(b) by 557 days.

(21) Appl. No.: 10/592,839

(22) PCT Filed: Mar. 9, 2005

(86) PCT No.: PCT/AU2005/000333
§ 371 (c)(1),
(2), (4) Date: Feb. 21, 2007

(87) PCT Pub. No.: WO2005/087139
PCT Pub. Date: Sep. 22, 2005

(65) Prior Publication Data
US 2008/0071364 A1 Mar. 20, 2008

Related U.S. Application Data

(60) Provisional application No. 60/559,784, filed on Apr. 6, 2004.

(30) Foreign Application Priority Data

Mar. 15, 2004 (AU) .................................. 2004901357

(51) Int. Cl.
*A61F 2/24* (2006.01)
(52) U.S. Cl. ....................................................... 623/2.11
(58) Field of Classification Search .................. 623/2.11, 623/2.36, 2.38, 2.39, 2.4, 1.36; 606/153
See application file for complete search history.

(56) References Cited

U.S. PATENT DOCUMENTS 4,018,229 A * 4/1977 Komiya .......................... 606/139
4,042,979 A * 8/1977 Angell .......................... 623/2.37
(Continued)

FOREIGN PATENT DOCUMENTS
EP 1 088 529 4/2001
(Continued)

OTHER PUBLICATIONS

Fukuda et al. "Three-Dimensional Geometry of the Tricuspid Annulus in Healthy Subjects and in Patients with Functional Tricuspid Regurgitation: A Real-Time, 3-Dimensional Echocardiographic Study." *Circulation: Journal of the American Heart Association* vol. 114. pp. 492-498.

(Continued)

*Primary Examiner* — (Jackie) Tan-Uyen T Ho
*Assistant Examiner* — Son Dang
(74) *Attorney, Agent, or Firm* — Merchant & Gould P.C.

(57) ABSTRACT

A device (1) for treating valve failure in a patient is provided. The device has one or more engaging zones (3) for engaging the device with the annulus of the valve being treated. The device also has pre-disposition means for changing the geometry of the device to a predetermined configuration which is suitable for constricting the valve annulus. The device is compressible for percutaneous delivery to the valve. When in the predetermined configuration, the engaged device constricts the valve annulus facilitating substantial closure of leaflets of the valve.

18 Claims, 4 Drawing Sheets

U.S. PATENT DOCUMENTS

| | | | |
|---|---|---|---|
| 5,061,277 A | 10/1991 | Carpentier et al. | |
| 5,477,864 A * | 12/1995 | Davidson | 600/585 |
| 5,716,416 A * | 2/1998 | Lin | 623/17.16 |
| 5,957,949 A * | 9/1999 | Leonhardt et al. | 623/1.24 |
| 6,165,183 A | 12/2000 | Kuehn et al. | |
| 6,174,332 B1 | 1/2001 | Loch et al. | |
| 6,254,636 B1 | 7/2001 | Peredo | |
| 6,312,447 B1 * | 11/2001 | Grimes | 606/219 |
| 6,419,696 B1 * | 7/2002 | Ortiz et al. | 623/2.37 |
| 6,425,916 B1 * | 7/2002 | Garrison et al. | 623/2.11 |
| 6,569,198 B1 | 5/2003 | Wilson et al. | |
| 6,800,090 B2 * | 10/2004 | Alferness et al. | 623/2.36 |
| 6,830,585 B1 * | 12/2004 | Artof et al. | 623/2.11 |
| 7,077,861 B2 * | 7/2006 | Spence | 623/2.11 |
| 7,101,395 B2 * | 9/2006 | Tremulis et al. | 623/2.11 |
| 7,371,259 B2 * | 5/2008 | Ryan et al. | 623/2.36 |
| 2001/0010017 A1 | 7/2001 | Letac et al. | |
| 2001/0014800 A1 | 8/2001 | Frazier et al. | |
| 2002/0002401 A1 | 1/2002 | McGuckin, Jr. et al. | |
| 2002/0087173 A1 | 7/2002 | Alferness et al. | |
| 2002/0095167 A1 * | 7/2002 | Liddicoat et al. | 606/151 |
| 2002/0123802 A1 * | 9/2002 | Snyders | 623/2.18 |
| 2002/0129820 A1 | 9/2002 | Ryan et al. | |
| 2002/0169504 A1 | 11/2002 | Alferness et al. | |
| 2003/0120340 A1 | 6/2003 | Liska et al. | |
| 2003/0153946 A1 | 8/2003 | Kimblad | |
| 2003/0171806 A1 | 9/2003 | Mathis et al. | |
| 2003/0181928 A1 | 9/2003 | Vidlund et al. | |
| 2003/0199974 A1 | 10/2003 | Lee et al. | |
| 2004/0039442 A1 * | 2/2004 | St. Goar et al. | 623/2.36 |
| 2004/0088047 A1 * | 5/2004 | Spence et al. | 623/2.36 |
| 2004/0133273 A1 * | 7/2004 | Cox | 623/2.11 |
| 2004/0138745 A1 | 7/2004 | Macoviak et al. | |
| 2004/0162610 A1 | 8/2004 | Liska et al. | |
| 2004/0167620 A1 * | 8/2004 | Ortiz et al. | 623/2.11 |
| 2004/0210305 A1 | 10/2004 | Shu et al. | |
| 2004/0243153 A1 * | 12/2004 | Liddicoat et al. | 606/151 |
| 2004/0243227 A1 | 12/2004 | Starksen et al. | |
| 2005/0107871 A1 * | 5/2005 | Realyvasquez et al. | 623/2.11 |
| 2005/0137686 A1 | 6/2005 | Salahieh et al. | |
| 2005/0143811 A1 | 6/2005 | Realyvasquez | |
| 2005/0177180 A1 | 8/2005 | Kaganov et al. | |
| 2007/0049942 A1 | 3/2007 | Hindrichs et al. | |
| 2008/0045977 A1 * | 2/2008 | To et al. | 606/139 |
| 2008/0082099 A1 * | 4/2008 | Dickens et al. | 606/42 |
| 2008/0140191 A1 * | 6/2008 | Mathis et al. | 623/2.37 |
| 2009/0276038 A1 * | 11/2009 | Tremulis et al. | 623/2.11 |
| 2010/0145440 A1 * | 6/2010 | Keranen | 623/2.37 |

FOREIGN PATENT DOCUMENTS

| | | |
|---|---|---|
| WO | WO 02/36048 | 5/2002 |
| WO | WO 03/017874 | 3/2003 |
| WO | WO 03/028558 A2 | 4/2003 |
| WO | WO 03/053289 A1 | 7/2003 |
| WO | WO 2004/019826 | 3/2004 |
| WO | WO 2004/019826 A1 | 3/2004 |
| WO | WO 2004/082538 | 9/2004 |
| WO | WO 2004/103223 A1 | 12/2004 |
| WO | WO 2004/112652 | 12/2004 |
| WO | WO 2005/046488 A2 | 5/2005 |
| WO | WO 2005/087139 | 9/2005 |

OTHER PUBLICATIONS

Ton-Nu et al. "Geometric Determinants of Functional Tricuspid Regurgitation: Insights from 3-Dimensional Echocardiography." *Circulation: Journal of the American Heart Association* vol. 114. pp. 143-149.

Nath et al. "Impact of Tricuspid Regurgitation on Long-Term Survival." *Journal of American College of Cardiology*. vol. 43, No. 3. 2004. pp. 405-409.

\* cited by examiner

TREATING VALVE FAILURE

This application is a national stage application under 35 U.S.C. §371 from PCT Application No. PCT/AU2005/000333, filed Mar. 9, 2005, which claims the priority benefit of Australian Application No. 2004901357, filed Mar. 15, 2004, and U.S. Provisional Application No. 60/559,784, filed Apr. 6, 2004.

FIELD OF THE INVENTION

The present invention relates to a method and apparatus for treating valve failure. In particular, the invention relates to a device and method for treating failure of valves of the heart including the tricuspid valve.

BACKGROUND TO THE INVENTION

The body's circulation is facilitated by the heart, the cardiac pump which ensures that fresh blood is supplied throughout the body delivering nutrients to organs and transporting waste products to the body's filtration systems. The heart, illustrated in section in FIG. 5, is a complex organ operating two pumping systems. One pumping system includes the left ventricle (LV) and left atrium (LA) and services the systemic circulation in which oxygenated blood is supplied to the body's organs. Deoxygenated blood is then returned to the right heart. The other pumping system includes the right ventricle (RV) and right atrium (RA) and services the pulmonary circulation, pumping deoxygenated blood from the heart to the lungs where it is re-oxygenated and then returned to the left heart for re-circulation to the body's organs.

Valves in the heart and throughout the body ensure that blood flows constantly in one direction. These include the mitral valve and the tricuspid valve, which separate the atria and ventricles of the left and right hearts respectively. The circulation is dependent on these valves to ensure that the blood is pumped continuously and efficiently through the heart and delivered to the rest of the body.

The tricuspid valve is a complex structure comprising leaflet tissue, chordae tendinae, papillary muscles and a supporting annulus. The tricuspid valve leaflets are a continuous veil of leaflet tissue that attach to the annulus. Three major leaflets are identified, anterior, septal and posterior. The annulus performs multiple functions including maintenance of valvular shape and dimensions.

In some cases, valves in the circulatory system such as the tricuspid and mitral heart valves are deficient or fail. The causes of partial or total heart valve failure include congenital/structural defects, disease and infection. However, the most common cause of valve failure is dilation of the valve annulus. This occurs as part of the generalised cardiac structural dilatation allied to cardiomyopathy and heart failure. The consequences of heart valve failure can vary depending on the seriousness of the failure, but in most cases the heart's efficiency and the efficiency of the circulatory system is seriously affected and complications often result.

Failure or leakage of the heart valves frequently results in mitral/tricuspid valve regurgitation. In the case of the mitral valve, regurgitation results in back pressure in the lungs, whereas tricuspid valve regurgitation can result in high back pressures in the venous circulation. Clearly, this is undesirable for the health of the heart, as well as for the lungs and other organs of the body. Mitral and tricuspid valve failure can lead to ineffective and/or inefficient cardiac pumping, ventricular and atrial enlargement, pulmonary and/or circulatory hypertension, heart failure and in some cases, death.

Methods exist for repairing and replacing cardiac valves and other valves of the body and treatments for mitral valve regurgitation in particular are available. One form of treatment involves replacement of the entire valve. In other cases, the mitral or tricuspid valve annulus may be repaired by placing a biocompatible annuloplasty ring inside the annulus and suturing the ring to the fibrous tissue of the annulus. In this case, the ring constricts the annulus, enabling the mitral or tricuspid valve leaflets to seal during each pumping cycle and reduce or prevent backflow.

Mitral valve replacement and implantation of the annuloplasty ring both require open heart surgery and are therefore major operations. The patient must be placed under general anaesthetic and undergo cardiopulmonary bypass. Concomitant with the seriousness of such procedures are an increase in morbidity and mortality risk, and a slow and painful period of rehabilitation which follows. Post-operative complications are also common and these include infection, thromboembolism, loss of ventricular function and a need for anticoagulation medication.

The implications of tricuspid valve regurgitation have not been well understood in the past and have only recently become a topic of interest. Because of this, the options available for patients experiencing tricuspid valve regurgitation are limited. The location of the tricuspid valve in the right heart complicates treatment because it is less easily accessible than the mitral valve, and it has a more complex triple-leaved structure.

The mitral valve is accessible via the coronary sinus/great cardiac vein (CS/GCV) which has a close anatomical relationship with the lateral border of the posterior annulus. The small cardiac vein has a similar relationship with the tricuspid annulus. However, unlike the CS/GCV, this vessel is small, variable in size and absent in approximately 50% of cases. Therefore, reasonable vascular access to the tricuspid annulus is limited to a right atrial approach.

In the light of the fact that the available forms of treatment for patients experiencing mitral and tricuspid valve regurgitation are high risk, expensive and prone to complications, it would be desirable to address the deficiencies of these approaches and develop a method of treating certain types of valve failure, particularly tricuspid valve failure, which is less expensive, less invasive, and therefore less likely to result in complications after the procedure.

The discussion of the background to the invention included herein is intended to explain the context of the present invention. It is not to be taken as an admission or a suggestion that any of the material referred to was published, known or part of the common general knowledge in Australia as at the priority date of any of the claims.

It is an object of the present invention to overcome or ameliorate one or more of the disadvantages of the prior art, or at least to provide a useful alternative.

SUMMARY OF THE INVENTION

In a first aspect of the present invention there is provided a device for treating valve failure in a patient, the device including:
(a) one or more engaging zones for engaging the device with a valve annulus of the valve being treated; and
(b) pre-disposition means for changing the geometry of the device to a predetermined configuration suitable for constricting the valve annulus;

wherein the device is compressible for percutaneous delivery to the valve, and wherein the engaged device, when in the predetermined configuration, constricts the valve annulus facilitating substantial closure of leaflets of the valve.

Embodiments of the invention may be suitable for treating a range of valves around the body. However, it is particularly desirable that the device is suitable for treating valves of the heart such as those separating the atria and ventricle and in particular, the tricuspid valve.

Preferably, the pre-disposition means is inherent in the material from which the device has been made. This may be in the form of a "shape memory" or other similar characteristic of the material wherein the shape memory corresponds to the predetermined configuration of the device. The predetermined configuration is preferably substantially annular with a diameter suitable for constricting the annulus in such a way that it aids closure of the leaflets of the valve. Alternatively, the pre-disposition means may be auxiliary to part of the device comprising the one or more engaging zones.

To avoid rejection from the body and/or infection or failure of the device, it is preferred that the device is made from a biocompatible material. Preferably, the biocompatible material includes a metal alloy. Desirable metal alloys include alloys of nickel and titanium. One such desirable metal alloy is nitinol, which has "shape memory" properties suitable for use as the pre-disposition means for changing the geometry of the device to the predetermined configuration.

Preferably, the device is expandable to substantially the same size as the untreated valve annulus to facilitate engagement of the one or more engaging zones with the valve annulus. The device may be expandable by way of struts or releasably engageable deployment apparatus configured to expand or stretch the device to substantially match the size and/or shape of the untreated valve annulus.

The engaging zones may take any suitable form. In one embodiment, one or more of the engaging zones includes a tooth for engaging the valve anulus. Alternatively or additionally one or more of the engagement zones may include a barb. Accordingly, the device may include a plurality of teeth and/or barbs along an edge of the device which contacts and engages with the valve annulus. On release or disengagement of the struts or deployment apparatus, the engaged device constricts to the predetermined configuration causing constriction of the engaged valve annulus also, thereby facilitating substantial closure of leaflets of the valve.

Preferably, the predetermined configuration substantially restores the geometry of the valve annulus. It is also preferable that the device is radially compressible by crushing or coiling the device upon itself. In one preferred embodiment, the device includes an open coil of nitinol tubing which can be torsionally compressed into a helix and released when appropriately located, relative to the valve annulus. In such an embodiment the engaging zones are in the form of teeth which are laser-cut in a surface of the tubing. As the tubing unravels, the teeth rotate outward enabling the tube to contact and therefore engage the device with the valve annulus.

In another preferred embodiment, the device is a closed coil of nitinol tubing which, when in the predetermined configuration, closely matches the desired shape of the annulus. When the device is compressed, it is radially compressed or "crushed" upon itself in such a way that it can be transported to the site of deployment percutaneously. The device is then deployed and expanded using struts, to contact and engage the annulus and is then constricted to its pre-determined configuration, thereby constricting the annulus.

In a second aspect of the present invention, there is provided a method of treating valve failure including the steps of:

(a) transporting a compressed valve repair device to a region of valve failure, said region including a valve annulus; and
(b) deploying the repair device by:
  (i) releasing the compressed repair device;
  (ii) engaging the released repair device with the valve annulus; and
  (iii) contracting the engaged repair device to a predetermined configuration;

wherein contraction of the engaged repair device to the predetermined configuration constricts the valve annulus thereby facilitating substantial closure of leaflets of the valve.

Preferably, the repair device is transported to the region of valve failure percutaneously. That is, using a catheter or other such lumen. Preferably the catheter or other lumen is sufficiently flexible to enter the patient's circulation through the skin and into the jugular vein or other suitable blood vessel and be directed to the tricuspid valve or other heart-valve being treated, or another valve of the body. Preferably, when the tricuspid valve is being treated, the device is transported to the tricuspid valve annulus through the atrium and deployed where the annulus forms a "shelf" on the atrial side of the valve.

In one preferred embodiment, the released repair device is expanded prior to engaging the repair device with the valve annulus. In such an embodiment it is preferred that the repair device is expanded to substantially the same size and/or shape as the untreated valve annulus, thereby facilitating engagement of the repair device with the valve annulus substantially evenly around the valve annulus. In one embodiment, the step of expanding the released repair device is facilitated by disengageable expanding means associated with a deployment apparatus. Such disengageable expanding means may be in the form of struts, hooks, a coil or other suitable means which can force the repair device to expand or "open up" to facilitate engagement of the device with the dilated valve annulus, and then be disengaged from the repair device after deployment, and safely removed from the patient.

It is preferable that the repair device is substantially annular in shape with one or more engaging zones. Preferably the annular shape substantially matches the geometry of the valve annulus being treated, and the predetermined configuration substantially matches the desired post-treatment geometry of the valve annulus. In one preferred embodiment, the device is engageable with the valve annulus by rotating the device in a first rotational direction (i.e. clockwise or counter-clockwise) whilst making contact with the inside the valve annulus, enabling the engaging zones which may be in the form of one or more teeth or barbs to engage with the annulus thereby securing the repair device in position.

Preferably the repair device is deployed from a repair device deployment apparatus which is introduced to the patient percutaneously via a suitable lumen such as a cardiac catheter. It is therefore desirable that the repair device is compressed whilst being delivered to the deployment site, and released from the compressed state once the repair device is deployed. In such an embodiment, deployment of the repair device from the deployment apparatus may occur by rotating the device in a second rotational direction (i.e. counter-clockwise or clockwise) so as to allow correct positioning of the repair device relative to the valve annulus before rotating in the opposite direction to engage the device with the annulus.

Prior to engaging the repair device with the valve annulus, it may be desirable to expand the repair device to facilitate better engagement of the engaging zones with the valve annulus. After the expanded repair device has been engaged with the valve annulus, it may then be constricted to the predetermined configuration.

In a third aspect of the present invention, there is provided apparatus for deploying a valve repair device in a patient, the apparatus including:

(a) positioning means to position the repair device relative to the valve;
(b) coupling means for releasably coupling the repair device to the positioning means; and
(c) releasably engageable expansion means configured to expand the repair device to substantially the same size as an untreated valve annulus;

wherein the positioning means and the coupling means are configured to deliver the repair device to a region of the valve through a percutaneous lumen and the releasably engageable expansion means is configured to expand the repair device to facilitate engagement of the repair device with an annulus of the valve being repaired.

Preferably the releasably engageable expansion means is released from the repair device and removed from the patient through the percutaneous lumen. This expansion facilitates engagement of one or more engaging zones of the repair device with the valve annulus. The releasably engageable expansion means may take any suitable form. In one embodiment, the expansion means include one or more struts associated with the coupling means and configured to expand the repair device so that it substantially matches the internal diameter of the untreated valve annulus.

Preferably the apparatus includes retaining means to retain the position of the repair device relative to the valve while the device is being expanded and/or engaged with the valve annulus. The retaining means may be a hook or anchor or a temporary guide wire with a helical screw at the tip or other suitable means capable of stabilising the device and deployment apparatus during deployment and implantation of the repair device and removed afterwards. This may occur by temporarily embedding the retaining means in an endocardial wall or the apex of the ventricle or other nearby tissue, without causing serious damage to that tissue.

BRIEF DESCRIPTION OF THE DRAWINGS

The present invention will now be described in greater detail with reference to the accompanying drawings. It is to be understood that the particularity of the accompanying drawings does not supersede the generality of the preceding description of the invention.

DETAILED DESCRIPTION

Figure 1A:
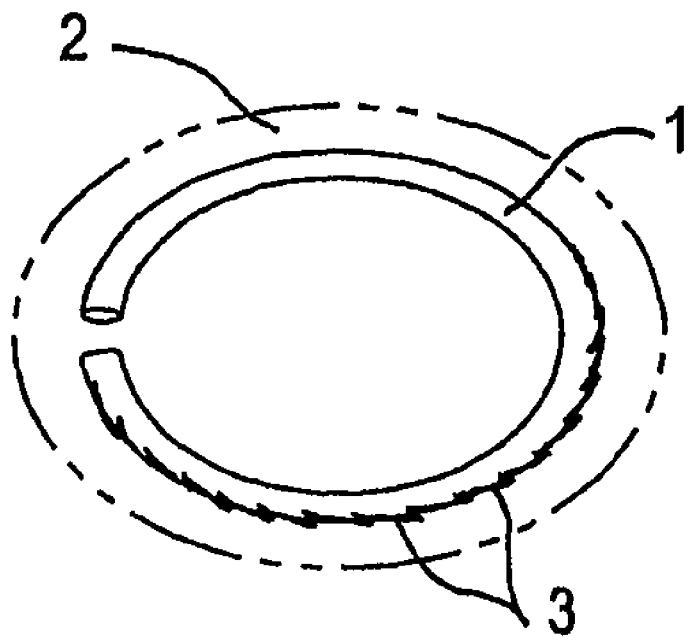
FIGS. 1A and 1B illustrate a device according to an embodiment of the invention, implanted in a valve annulus.

Referring firstly to FIG. 1A there is shown a device (generally shown as 1) for treating failure of a valve such as the tricuspid or mitral valve of the heart. The device includes one or more engaging zones 3 for engaging the device with the valve annulus 2, the fibrous ring of tissue from which the leaflets of the valve extend. The device also includes pre-disposition means which, in a preferred embodiment of the invention, is inherent in the material from which the device is manufactured. In such an embodiment, the material is preferably nitinol, a shape memory alloy which can be "programmed" to have a pre-determined configuration when situated, unconfined, in an environment having a particular temperature. Implantation in the human body (or other animal body) is one such environment in which devices formed from nitinol or equivalent material exhibit these "shape memory" characteristics, realising their pre-determined configuration.

In one preferred embodiment, the device 1 is formed from a piece of nitinol tubing which has a shape memory that corresponds to a predetermined configuration suitable for constricting the valve annulus 2. The shape memory is obtained using treatment by lowering the temperature of the nitinol coil and using a "salt pot" as is known in the art. An approximation of one such suitable shape is illustrated in FIG. 1A.

After treatment to program the nitinol tubing with its "shape memory", the tubing can be manipulated when nitrogen-cooled to a very low temperature and compressed or wound upon itself to form a helix. Compression of the device in this manner enables it to be inserted into a lumen with a small bore which facilitates percutaneous delivery to the valve for implantation. One suitable form of lumen is a catheter 7 as illustrated in FIGS. 2 and 3.

Figure 1B:
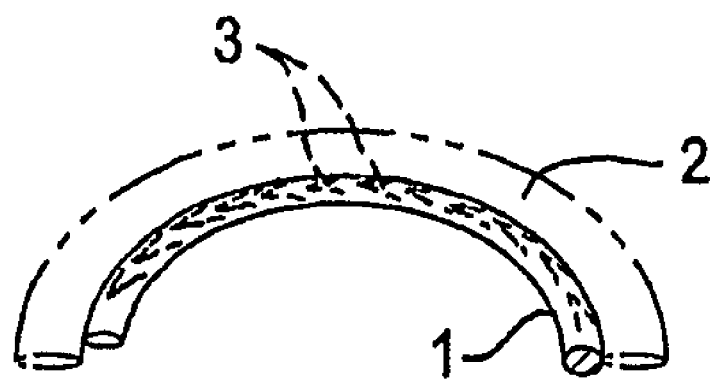
Figure 2:
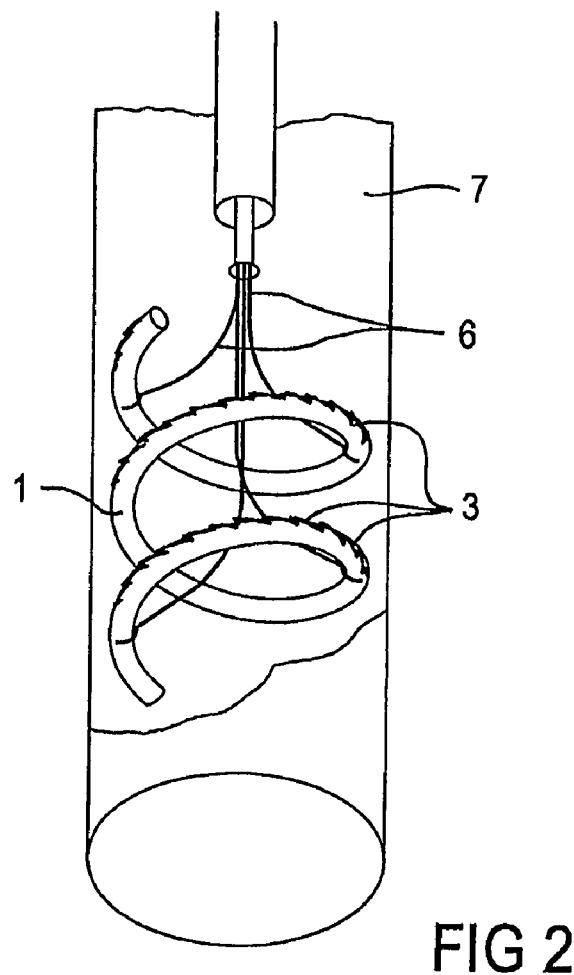
FIG. 2 illustrates a device according to an embodiment of the invention in a compressed state, inside a percutaneous delivery lumen.
Figure 3:
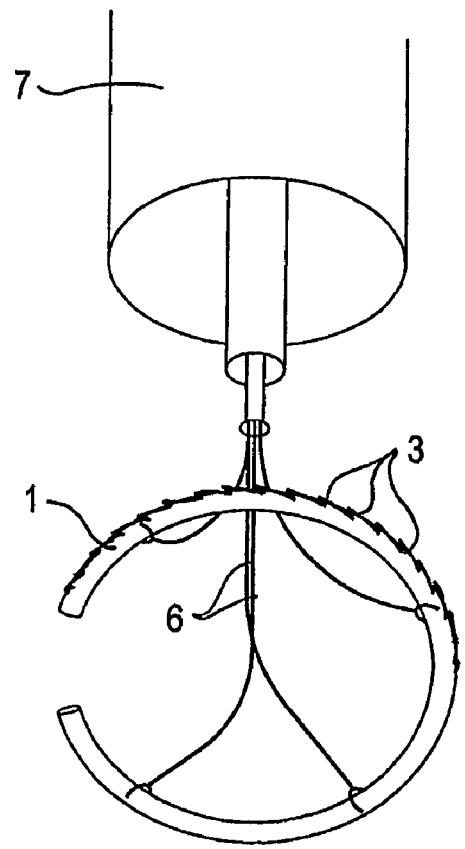
FIG. 3 illustrates the device of FIG. 2 in an expanded state, showing releasably engageable expansion means.

FIG. 2 shows the device 1 of FIGS. 1A and 1B in a compressed form for percutaneous delivery to the valve using a cardiac catheter 7 or other suitable lumen. When the device is released from catheter 7 it will "spring" back to its shape memory configuration upon reaching a temperature range which includes body temperature. After implantation, the device will retain its pre-determined configuration or shape memory whilst engaged with the valve annulus 2, thereby constricting the annulus to a geometry which facilitates substantial closure of the leaflets of the valve.

Preferably, the engagement zones 3 are teeth which have been laser cut into the tubing forming a type of "barbed spring" when the tubing is in the compressed state. When the compressed device is released from catheter 7 at the site of the valve, it relaxes to its predetermined configuration and the surface of the tubing rotates outward causing the teeth to engage with the annulus 2. Preferably, components of the apparatus required to perform the procedure (i.e. position and engage the device) are deployed over a guide wire (not shown) if necessary and though the catheter 7 to the site of valve repair, along with the device itself. Use of a guide wire system is desirable to assist location and orientation of the device, relative to the valve and the valve annulus.

A guiding system may be used to orient the device and to deploy it in position, so that it engages with the valve annulus. Preferably, engagement of the device with the valve annulus occurs on the shelf of tissue comprising part of the annulus on the atrial side of the tricuspid valve. In one embodiment, the guide wire may include anchor means to engage tissue proximal (preferably just below) the annulus to reduce movement of the deployment apparatus and hence the device relative to the valve annulus during implantation of the device (i.e. before the device is engaged with the valve anulus).

In a preferred embodiment, catheter 7 comprises part of a deployment apparatus. In the embodiment shown in FIG. 2, the deployment apparatus also includes expansion means shown in the form struts 6 which are used to expand the device 1 once it has been ejected from catheter 7 and released from the compressed state. Struts 6 increase the device's diameter to greater than that of the predetermined configuration and substantially match that of the untreated valve annulus. This enables engagement zones 3 to be more evenly distributed around the internal surface of annulus 2 and improves the evenness with which the valve annulus is constricted after implantation of the device. The expanded device 1 is shown in FIG. 3. Struts 6 may be manipulated by a surgeon or physician performing the treatment, and released from the device once the device has been engaged with the anulus for removal from the patient through catheter 7.

It may be possible to engage the device with the valve annulus without expanding the device. With care and skill, the device 1 may be moved relative to the annulus 2 in such a way that the engaging zones engage parts of the annulus to form pleats or gathers around the annulus. This may result in a substantially even distribution of the constriction force. It is to be understood that other suitable engagement means may be provided, along with other suitable alternatives for the expansion means which, in the embodiments illustrated, are provided in the form of struts 6.

For treatment of the tricuspid valve, it is preferred that catheter 7 enters the body through the jugular vein and snakes its way into the superior vena cava and right atrium to access the tricuspid valve annulus. Surgeons or physicians performing the procedure may use any suitable imaging technique to assess the region of the valve annulus and position and engage the valve repair device and deployment apparatus. X-ray fluoroscopy is one imaging technique which may be used to assist in accurately positioning the device. Alternatively or additionally, surgeons and physicians may use haptic feedback and/or ancillary devices delivered to the region via catheter 7 to position and engage the device 1 relative to the valve annulus 2.

Figure 4:
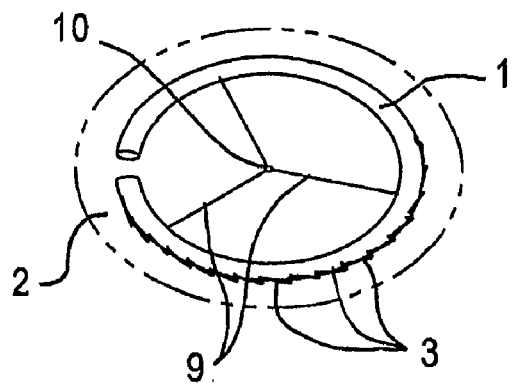
FIG. 4 illustrates an alternative embodiment of the invention wherein the pre-disposition means is provided in the form of struts connected so as to maintain the predetermined configuration of the device.
Figure 5:
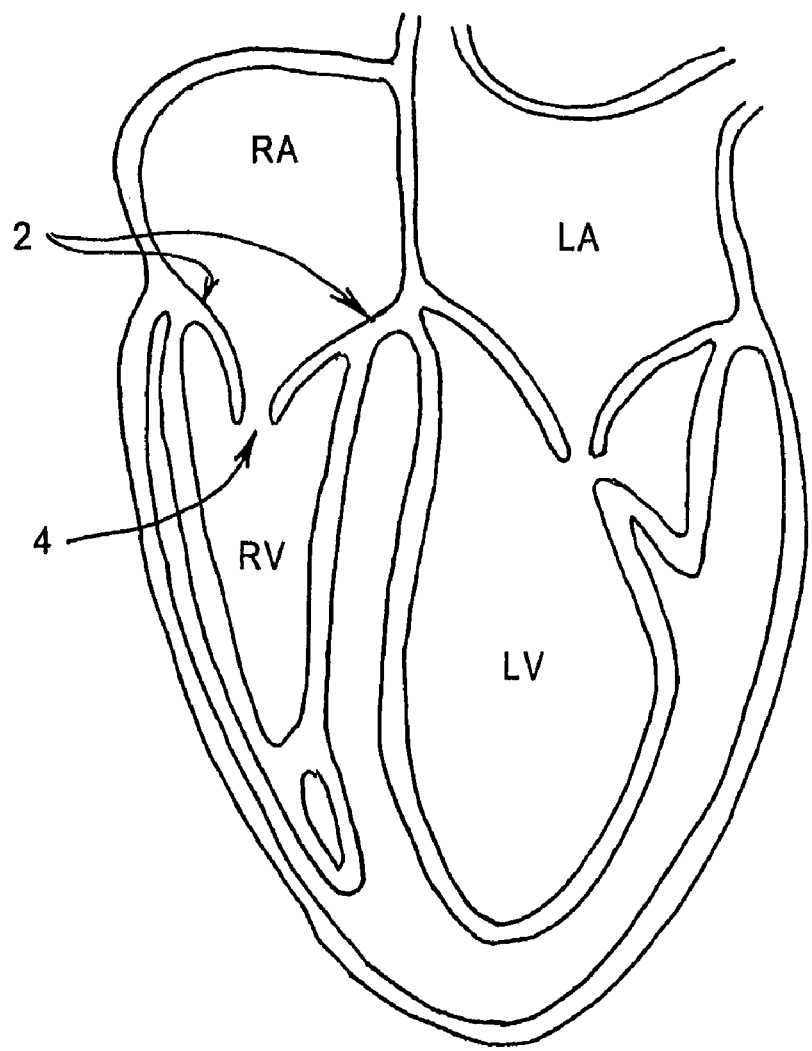
FIG. 5 illustrates a simplified cross section of the heart.

FIG. 4 illustrates an alternative embodiment of the invention in which the pre-disposition means is provided in the form of three struts 9 connected in such a way that they maintain the predetermined configuration of the device. These struts may be connected at nexus 10 to facilitate adjustment of the device by, say turning clockwise or counter clockwise to increase or decrease the effective diameter of the device and therefore engage and constrict the annulus.

Figure 6A:
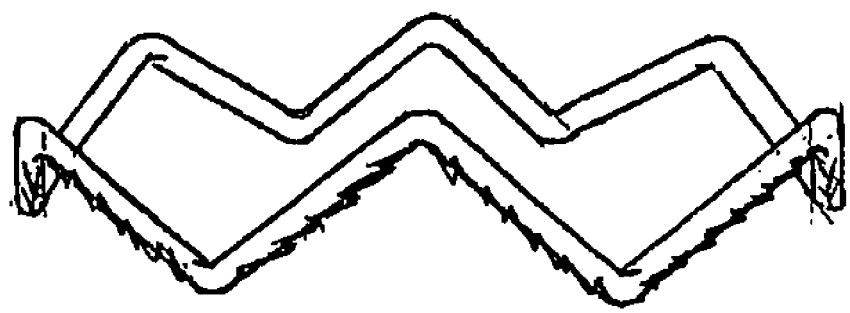
FIGS. 6A and 6B illustrate an alternative valve repair device according to another embodiment of the invention.
Figure 6B:
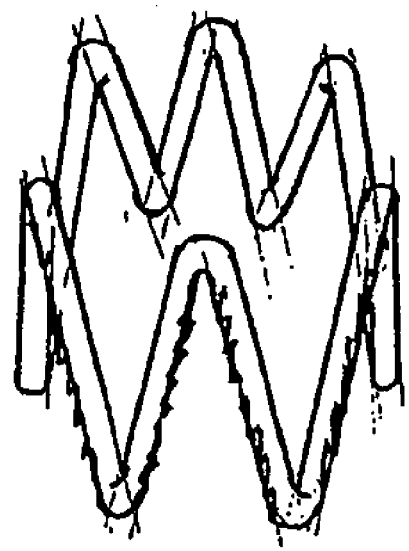

A further embodiment of the invention is illustrated in FIGS. 6A and 6B. In this embodiment, the valve repair device is a closed ring, rather than an open one, and is radially compressed by "crushing" the ring upon itself. This embodiment of the device is illustrated in its pre-determined configuration in FIG. 6A and in its compressed state in FIG. 6b. The compressed device is suitable for percutaneous delivery to the site of deployment via lumen 7.

Advantageously, a patient having a valve treated using embodiments of the present invention does not require general anaesthetic. Rather, he or she can be treated with the valve being accessed percutaneously while the patient is sedated. Clearly, this is beneficial to the patient as the recovery time is significantly reduced and the device could be implanted during an out-patient procedure. Use of a sedative also reduces the risk of mortality which is associated with use of general anaesthetic in elderly patients. Percutaneous treatment of valve failure according to the invention eliminates the need for open heart surgery which has previously been required for treating heart valve failure and this clearly enables patients treated according to the invention to recover more quickly with reduced risk of infection, surgical complications and mortality, and the discomfort which accompanies open heart or other major surgery.

It is to be understood that materials suitable for manufacturing the inventive device are not intended to be limited to nitinol or other alloys of nickel and titanium. Rather, the scope of the invention is intended to encompass devices manufactured from any suitable biocompatible material or combination of materials. Such materials may include stainless steels, ceramics and synthetic materials which can be changed in configuration to facilitate percutaneous delivery to the valve and realise a predetermined configuration which facilitates constriction of the valve annulus. Whilst in most cases it would be desirable to restrict the annulus in such a way that a healthy annulus geometry is restored, in many serious cases of heart valve failure it may be sufficient to achieve an annulus reduction of 20% or less to restore a degree of valve function and thereby improve the quality of life of the patient. Another desirable advantage of implantation of such a device is prevention of further dilation of the valve annulus.

Implantation of the valve repair device need not be limited to valves of the heart. It may also be desirable to repair degradation or dilation of the annulus of other valves around the body so as to treat or reduce valvular regurgitation in the vessels affected. Other valves for which the invention may be suitable may include but are not limited to the valves of the oesophagus, urinary tract and intestinal tract.

It is to be understood that various modifications, additions and/or alterations may be made to the parts previously described without departing from the ambit of the present invention as defined in the claims appended hereto.

The invention claimed is:

1. A device for treating valve failure in a patient, the device having:
    (a) one or more engaging zones for engaging the device with a valve annulus of the valve being treated;
    (b) pre-disposition means for changing the geometry of the device to a predetermined configuration suitable for constricting the valve annulus; and
    (c) releasably engageable expansion means including one or more struts configured to expand the periphery of the device to substantially match the internal diameter geometry of the valve annulus
    wherein the device is compressible within a delivery lumen for percutaneous delivery to the valve, and wherein the one or more struts facilitate expansion of the device when released from the delivery lumen to facilitate engagement of one or more engaging zones of the device with the untreated valve annulus, and wherein upon release of the one or more struts the device assumes the predetermined configuration and constricts the valve annulus facilitating substantial closure of leaflets of the valve.

2. A device for treating valve failure according to claim 1 wherein the device when released from the delivery lumen, is expandable to substantially match the geometry of the untreated valve annulus to facilitate engagement of the one or more engaging zones with the valve annulus, and capable of returning to the predetermined configuration.

3. A device for treating valve failure according to claim 1 wherein the device is made from a biocompatible material and the pre-disposition means includes a shape memory inherent in the material, said shape memory corresponding to the predetermined configuration.

4. A device for treating valve failure according to claim 3 wherein the biocompatible material includes a metal alloy.

5. A device for treating valve failure according to claim 4 wherein the alloy includes nickel and titanium.

6. A device for treating valve failure according to claim 1 wherein one or more of the engaging zones includes a tooth for engaging the valve annulus.

7. A device for treating valve failure according to claim 1 wherein one or more of the engaging zones includes a barb.

8. A device for treating valve failure according to claim 1 wherein the device is substantially annular and torsionally compressible for percutaneous delivery to the valve by coiling the device upon itself within the delivery lumen.

9. A device for treating valve failure according to claim 1 wherein the device is substantially annular and radially compressible within the delivery lumen for percutaneous delivery to the valve.

10. A device for treating valve failure according to claim 1 wherein the device is a nitinol coil and the engaging zones include laser-cut teeth formed in a surface of the device, said surface being configured to engage with the valve annulus.

11. A device for treating valve failure according to claim 1 wherein the valve being treated is a valve of the heart.

12. A device for treating valve failure according to claim 1 wherein the heart valve is the tricuspid valve.

13. Apparatus for deploying a valve repair device in a patient, the apparatus including:
   (a) positioning means to position the repair device relative to the valve;
   (b) coupling means for releasably coupling the repair device to the positioning means; and
   (c) releasably engageable expansion means including one or more struts configured to expand the periphery of the repair device to substantially match the internal diameter geometry of the untreated valve annulus;
   wherein the repair device comprises a pre-disposition means for changing the geometry of the device to a predetermined configuration suitable for constricting the valve annulus, and
   wherein the positioning means and the coupling means are configured to deliver the repair device to a region of the valve within a percutaneous delivery lumen and wherein after delivery of the valve repair device from the delivery lumen the releasably engageable expansion means facilitates engagement of one or more engaging zones of the repair device with the valve annulus.

14. Apparatus for deploying a valve repair device according to claim 13 in combination with a valve repair device that is coupled by said coupling means to said positioning means where the device comprises one or more engaging zones for engaging the device with a valve annulus of the valve being treated.

15. A device for treating valve failure according to claim 1 wherein the device comprises Nitinol tubing having engaging zones in the form of teeth, and having helical shape when compressed within the delivery lumen for percutaneous delivery to the valve, wherein when released from the delivery lumen, the teeth rotate outward to engage the valve annulus.

16. A device for treating valve failure according to claim 1 further including retaining means selected from the group comprising a hook, anchor or screw for engaging tissue in the vicinity of the valve and adapted to maintain the position of the repair device when attached to the valve annulus.

17. A device for treating valve failure according to claim 1, the device having annular shape and compressible for percutaneous delivery by inwardly collapsing the device to fit within the delivery lumen.

18. The combination of claim 14, wherein the apparatus is adapted to deploy the valve repair device from a delivery lumen by rotating the device in a first direction and is adapted to engage the engaging zones of the deployed device with the annular tissue by rotating the device in a second direction.

\* \* \* \* \*